US006989387B2

(12) United States Patent
LaVoie et al.

(10) Patent No.: US 6,989,387 B2
(45) Date of Patent: Jan. 24, 2006

(54) NITRO AND AMINO SUBSTITUTED TOPOISOMERASE AGENTS

(75) Inventors: Edmond J. LaVoie, Princeton Junction, NJ (US); Sudhir K. Singh, Bangalore (IN); Leroy F. Liu, Bridgewater, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 10/638,944

(22) Filed: Aug. 11, 2003

(65) Prior Publication Data
US 2004/0110760 A1 Jun. 10, 2004

Related U.S. Application Data

(60) Provisional application No. 60/402,138, filed on Aug. 9, 2002.

(51) Int. Cl.
*A61K 31/4738* (2006.01)
*C07D 491/12* (2006.01)

(52) U.S. Cl. .......................... 514/280; 546/48; 546/70; 544/233; 514/248; 514/285; 435/184

(58) Field of Classification Search ................. 514/285, 514/280, 248; 546/70, 48; 544/233; 435/184
See application file for complete search history.

(56) References Cited

U.S. PATENT DOCUMENTS

| | | | |
|---|---|---|---|
| 2,915,523 A | 12/1959 | Moore et al. | |
| 2,981,731 A | 4/1961 | Moore et al. | |
| 2,985,661 A | 5/1961 | Hien et al. | |
| 3,267,107 A | 8/1966 | Sallay | |
| 3,272,707 A | 9/1966 | Tedeschi | |
| 3,449,330 A | 6/1969 | Guglielmetti et al. | |
| 3,538,097 A | 11/1970 | Lowe et al. | |
| 3,542,782 A | 11/1970 | Houlihan et al. | |
| 3,849,561 A | 11/1974 | Junzo et al. | |
| 3,884,911 A | 5/1975 | Shimada et al. | |
| 3,912,740 A | 10/1975 | Zee-Chang et al. | |
| 4,559,157 A | 12/1985 | Smith et al. | 252/90 |
| 4,608,392 A | 8/1986 | Jacquet et al. | 514/844 |
| 4,749,708 A | 6/1988 | Maroko | |
| 4,761,417 A | 8/1988 | Maroko | |
| 4,761,477 A | 8/1988 | Ikekawa et al. | |
| 4,820,508 A | 4/1989 | Wortzman | 424/59 |
| 4,925,943 A | 5/1990 | Kanmacher et al. | |
| 4,938,949 A | 7/1990 | Borch et al. | 514/476 |
| 4,980,344 A | 12/1990 | Maroko | |
| 4,992,478 A | 2/1991 | Geria | 514/782 |
| 5,106,863 A | 4/1992 | Hajos et al. | |
| 5,112,532 A | 5/1992 | Ninomiya et al. | |
| 5,126,351 A | 6/1992 | Luzzio et al. | |
| 5,153,178 A | 10/1992 | Maroko | |
| 5,190,753 A | 3/1993 | Behrens et al. | |
| 5,244,903 A | 9/1993 | Wall et al. | |
| 5,318,976 A | 6/1994 | Luzzi et al. | |
| 5,639,759 A | 6/1997 | Magolda et al. | |
| 5,646,283 A | 7/1997 | Suzuki et al. | |
| 5,767,142 A | 6/1998 | LaVoie et al. | |
| 5,770,617 A | 6/1998 | LaVoie et al. | |
| 5,807,874 A | 9/1998 | LaVoie et al. | |
| 5,981,541 A | 11/1999 | LaVoie et al. | |
| 6,140,328 A | 10/2000 | LaVoie et al. | 514/248 |
| 6,509,344 B1 | 1/2003 | Cushman et al. | |
| 6,740,650 B2 | 5/2004 | LaVoie et al. | |
| 2004/0110760 A1 | 6/2004 | LaVoie et al. | |
| 2005/0009824 A1 | 1/2005 | LaVoie et al. | |
| 2005/0009825 A1 | 1/2005 | Lavoie et al. | |
| 2005/0009826 A1 | 1/2005 | LaVoie et al. | |

(Continued)

FOREIGN PATENT DOCUMENTS

EP 0108147 B1 5/1984

(Continued)

OTHER PUBLICATIONS

Singh, S.K. et al.: Nitro and amino substitution in the D-ring of 5-(2-dimethylaminoethyl)-2,3-methylenedioxy-5H-dibenzo[c,h][1,6]naphthyridin-6-ones. J. Med. Chem. vol. 46, pp. 2254-2257, 2003.*

(Continued)

*Primary Examiner*—Charanjit S. Aulakh
(74) *Attorney, Agent, or Firm*—Viksnins Harris & Padys PLLP

(57) ABSTRACT

The invention provides compounds of formula I:

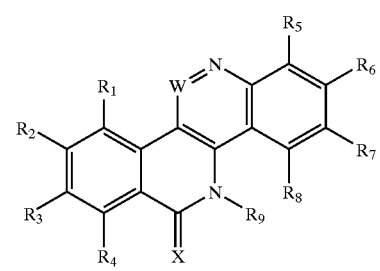

wherein $R_1$–$R_9$, W, and X have any of the meanings defined in the specification and their pharmaceutically acceptable salts. The invention also provides pharmaceutical compositions comprising a compound of formula I, processes for preparing compounds of formula I, intermediates useful for preparing compounds of formula I, and therapeutic methods for treating cancer using compounds of formula I.

58 Claims, 2 Drawing Sheets

U.S. PATENT DOCUMENTS

2005/0010046 A1    1/2005    LaVoie et al.

FOREIGN PATENT DOCUMENTS

| EP | 0496634 A1 | 7/1992 |
| GB | 2108955 A | 5/1983 |
| RU | 1530628 | 12/1989 |
| WO | WO-92/21661 A1 | 12/1992 |
| WO | WO-96/36612 A1 | 11/1996 |
| WO | WO-97/29106 A1 | 8/1997 |
| WO | WO-98/12181 A1 | 3/1998 |
| WO | WO-98/31673 A1 | 7/1998 |
| WO | WO-99/31067 A1 | 6/1999 |
| WO | WO-00/21537 | 4/2000 |
| WO | WO-01/32631 A2 | 5/2001 |
| WO | WO-03/041660 A2 | 5/2003 |
| WO | WO-03/047505 A2 | 6/2003 |
| WO | WO-2004/014918 A1 | 2/2004 |

OTHER PUBLICATIONS

Andoh, T , et al., "Drug resistance mechanisms of topoisomerase I drugs", *Advances in Pharmacology*, 29B, (1994), 93-103.

Carmichael, J, "Evaluation of a tetrazolium-based semiautomated colorimetric assay: assessment of chemosensitivity testing", *Cancer Research*, 47(4), (Feb. 15, 1987),936-42.

Chen, Allan Y., "A New Mammalian DNA Topoisomerase I Poison Hoechst 33342: Cytoxicity and Drug Resistance in Human Cell Cultures", *Cancer Research*, 53(6), (Mar. 15, 1993), 1332-1337.

Denizot, F., "Rapid colormetric assay for cell growth and survival—Modifications to the tetrazolium dye procedure giving improved sensitivity and reliability", *Journal of Immunological Methods*, 89 (2), (May 22, 1986),271-277.

Fujii, Noboru, et al., "Induction of Mammalian DNA Topoisomerase I-mediated DNA Cleavage and DNA Winding by Bulgarein", *Journal of Biological Chemistry*, 268 (18), (Jun. 25, 1993), 13160-13165.

Gatto, Barbara, "Identification of Topoisomerase I as the Cyctotoxic Target of the Protoberberine Alkaloid Coralyne", *Cancer Research*, 56(12), (Jun. 15, 1996),2795-2800.

Kim, Jung S., "Substituted 2,5'-Bi-1H-benzimidazoles: Topoisomerase I Inhibition and Cytotoxicity", *Journal of Medicinal Chemistry*, 39(4), (Feb. 16, 1996), 992-998.

Makhey, Darshan, "Coralyne and Related Compounds as Mammalian Topoisomerase I and Topoisomerase II Poisons", *Bioorganic & Medicinal Chemistry*, 4(6), (Jun. 1996),781-791.

Makhey, Darshan, "Protoberberine Alkaloids and Related Compounds as Dual Inhibitors of Mammalian Topoisomerase I and II", *Medicinal Chemistry Research* , 5(1), (1994), 1-12.

Maniatis, Tom, "Molecular cloning :a laboratory manual", *Cold Spring Harbor, N.Y.: Cold Spring Harbor Laboratory*, (1982), 149-185.

Mosmann, T., "Rapid Colorimetric Assay for Cellular Growth and Survival: Application to Proliferation and Cytotoxicity Assays", *Journal of Immunological Methods*, 65(1-2), (Dec. 16, 1983),55-63.

Singh, S. K., et al., "Nitro and Amino Substitution in the D-Ring of 5-(2-Dimethylaminoethyl)-2,3-methylenedioxy-5H-dibenzo [c,h] [1,6] naphthyridin-6-ones: Effect on Topoisomerase-I Targeting Activity and Cytotoxicity", *Journal of Medicinal Chemistry* 46(11), (2003),2254-2257.

Stermitz, Frank R., "Synthesis and Biological Activity of Some Antitumor Benzophenanthridinum Salts", *Journal of Medicinal Chemistry*, 18(7), (Jul. 1975),708-713.

Sun, Q , et al., "Synthesis and evaluation of terbenzimidazoles as topoisomerase I inhibitors", *Journal of Medicinal Chemistry*, 38(18), (Sep. 1, 1995), 3638-44.

Tewey, K M., et al., "Adriamycin-induced DNA damage mediated by mammalian DNA topoisomerase II", *Science*, 226(4673), (Oct. 26, 1984), 466-8.

Wang, H , et al., "Stimulation of topoisomerase II-mediated DNA damage via a mechanism involving protein thiolation", *Biochemistry*, 40(11), (Mar. 20, 2001),3316-23.

Yamashita, Yoshinori , et al., "Induction of Mammalian DNA Topoisomerase I and II Mediated DNA Cleavage by Saintopin, a New Antitumor Agent from Fungus", *Biochemistry*, 30(24), (Jun. 18, 1991),5838-5845.

Yamashita, Yoshinori , "Induction of Mammalian DNA Topoisomerase I Mediated DNA Cleavage by Antitumor Indolocarbazole Derivatives", *Biochemistry*, 31(48), (Dec. 8, 1992), 12069-12075.

Akiyama, Shin-Ichi , et al., "Isolation and Genetic Characterization of Human KB Cell Lines Resistant to Multiple Drugs", *Somatic Cell and Molecular Genetics*, 11(2), (1985), 117-126.

Andoh, Toshiwo , et al., "Characterization of a mammalian mutant with a camptothecin-resistant DNA topoisomerase I", *Proceedings of the National Academy of Sciences USA*, 84(16), (1987),5565-5569.

Aquirre, J. M., et al., "Reaction of 1,2-diarylethylamides with ethyl polyphosphate(EPP): correlation of the von Braun, Ritter and Bischler-Napieralski reactions.", *Chemical Abstracts*, 111(13), Abstract No. 115004, (1989),646.

Arumugam, N. , et al., "Synthesis of 7,8-Benzophenanthridines", *Indian Journal of Chemistry*, vol 12, (1974),664-667.

Badia, Dolores , et al., "Silicon-mediated isoquinoline synthesis: preparation and stereochemical characterization of 4-hydroxy-3-phenylisoquinolines", *Chemical Abstracts*, 117(13), Abstract No. 131034,(1992),730.

Baezner, C. , et al., "Uberfuhrung von o-nitro- und o,p-dinitro-benzylchlorid in acridinderivate", *Berichte der Deutschen Chemischen Gesellschaft*, 39, English Title—Conversion of i-nitro and o,p-dinitrobenzylchlroide into acridinic derivatives,(1906),2438-2447.

Baezner, Carlo , "Uberfuhrung von o-nitround o, p-dinitrobenzylchlorid in acridinderivate", *Berichte der Deutschen Chemischen Gesellschaft*, 37, English Title—Conversion of o-nitrobenzyl chloride and o,p-dinitrobenzyl chloride into acridine derivatives,(1904),3077-3083.

Bhakuni, D. S., et al., "Protoberberine Alkaloids", *The Alkaloids*, vol. 28, Chapter 2, Academic Press, Inc.,(1986), 95-181.

Bjornsti, Mary-Ann , et al., "Expression of human DNA topoisomerase I in yeast cells lacking yeast DNA topoisomerase I: restoration of sensitivity of the cells to the antitumor drug camptothecin", *Cancer Research*, 49, (1989), 6318-6323.

Bradsher, Charles K., et al., "alpha-Acyl-o-totunitriles as intermediates in the preparation of 3-substituted isoquinolines and 1-amino-2-benzopyrylium derivatives", *Chemical Abstracts*, 89(21), Abstract No. 89: 179810b, (1978),590.

Brossi, Arnold , "Antitumor Alkaloids", *The Alkaloids, Chemistry and Pharmacology*, vol. XXV, Academic Press, Inc.,(1985), 178-199.

Buu-Hoi, N. P., et al., "Carcinogenic Nitrogen Compounds. XV. Polysubstituted Angular Benacridines and Benzophenarsafzines", *Chemical Abstracts*, 49(1), Abstract, Column 330, 10-Organic Chemistry,(1955),329-330.

Buu-Hoi, Ng , et al., "The Chemistry of Carcinogenic Nitrogen Compounds. Part X. The Pfitzinger Reaction in the Synthesis of 1:2-Benzacridines", *Journal of the Chemical Society, Letchworth, GB*, (1952),279-281.

Buu-Hoi, Ng , "The chemistry of carcinogenic nitrogen compounds. Part V. Angular hydroxybenzacridines and hydroxydibenzacridines", *Journal of the Chemical Society, Letchworth GB*, (1950),2096-2099.

Chen, Allan Y., et al., "DNA Minor Groove-Binding Ligands: A Different Class of Mammalian DNA Topoisomerase I Inhibitors", *Proceedings of the National Academy of Sciences of the United States of American*, 90, (1993),8131-8135.

Chen, Allan Y., et al., "DNA Topoisomerase: Essential Enzymes and Lethal Targets", *Annu. Rev. Pharmacol. Toxicol.*, 34, (1994), 191-218.

Cherif, Abdallah , et al., "N-(5,5-Diacetoxypent-1-yl) doxorubicin: a new intensely potent doxorubicin analogue", *Journal of Medicinal Chemistry*, 35, (Aug. 21, 1992),3208-3214.

Croisy-Delcey, M. , et al., "Synthesis and Carcinogenic Activity of Oxidized Benzacridines: Potential Metabolites of the Strong Carcinogen 7-methylbenz[c]acridine and of the Inactive Isomer 12-methylbenz[a]acridine", *Chemical Abstracts*, 98, Abstract No. 43798, (1983),27-29.

Croisy-Delcey, M. , et al., "Synthesis and carcinogenic activity of oxidized benzacridines: potential metabolites of the strong carcinogen 7-methylbenz[c]acridine and of the inactive isomer 12-methylbenz[a]acridine.", *Journal of Medicinal Chemistry*, 26, (1983),303-306.

Cushman, Mark , et al., "Synthesis and antitumor activity of structural analogues of the anticancer benzophenanthridine alkaloid fagaronine chloride", *Journal of Medicinal Chemistry*, 28, (1985), 1031-1036.

Cushman, Mark , et al., "Synthesis of New Indeno[1,2-c] isoquinolines: Cytotoxic Non-Camptothecin Topoisomerase I Inhibitors", *Journal of Medicinal Chemistry*, 43(20), (2000),3688-3698.

D'Arpa, Peter , et al., "Topoisomerase-targeting antitumor drugs", *Biochimica et Biophysica Acta*, 989, (1989), 163-177.

Denny, W. A., "Emerging DNA Topoisomerase Inhibitors as Anticancer Drugs", *Expert Opin. Emerg. Drugs*, 9 (1), (2004), 105-133.

Dominguez, Esther, et al., "Dehydrogenation reactions of 1-substituted-3-aryltetahydroisoquinoline derivatives", *Chemical Abstracts*, 101(11), Abstract No. 090742z,(1984), 624.

Dorofeenko, G. N., et al., "Synthesis of 3-aryl derivatives of 2-benzopyrylium salts with free.alpha.-positions", *Chemical Abstracts*, 74 (15), Abstract No. 076295,(1971), 1013-1014.

Fitzgerald, J. J., et al., "Reaction of benzocyclobutene oxides with nitriles: synthesis of hypecumine and other 3-substituted isoquinolines", *Chemical Abstracts*, 122(7), Abstract No. 081704,(Feb. 13, 1995), 1128.

Fox, G. J., et al., "para-Bromination of Aromatic Amines: 4-Bromo-N,N-Dimethyl-3-(Trifluoromethyl)Aniline", *Organic Syntheses*, vol. 55, (1976),20-23.

Gallo, Robert C., et al., "Studies on the Antitumor Activity, Mechanism of Action, and Cell Cycle Effects of Camptothecin", *Journal of the National Cancer Institute*, vol. 46, No. 4, (1971),pp. 789-795.

Garcia, Alberto , et al., "A simple direct approach to 1-substituted 3-arylisoquinolines from deoxybenzoins and nitriles", *Chemical Abstracts*, 110(25), Abstract No. 231407u,(Jun. 19, 1989),662.

Giovanella, Beppino C., et al., "Complete growth inhibition of human cancer xenografts in nude mice by treatment with 20-(S)-camptothecin", *Cancer Research*, 51(11), (Jun. 1, 1991),3052-3055.

Godowski, K. C., et al., "Free amine benzophenanthridine alkaloid compositions", *USPATFULL Database, No. 95: 20510, RN No. 218-38-2 (Benzo[c]phenanthradine)*, from U.S. Patent 5,395,615, (Mar. 7, 1995),3 pages.

Goldman, Gustavo H., et al., "Differential poisoning of human and Aspergillus nidulans DNA topoisomerase I by bi- and terbenzimidazoles", *Biochemistry*, 36(21), (1997), 6488-6494.

Gopinath, K. W., et al., "Synthesis of Some 1:2- and 7:8-Benzophenanthridines", *Journal of the Chemical Society*, 78(2), (1958),504-509.

Hahn, F. E., et al., "Berberine", *In: Antibiotics, Mechanism of Action of Antimicrobial and Antitumor Agents*, vol. III, J. W. Corcoran, et al., (eds.), Springer-Verlag, (1975),577-584.

Halligan, Brian D., et al., "Purification and Characterization of a Type II DNA Topoisomerase from Bovine Calf Thymus", *The Journal of Biological Chemistry*, 260(4), (Feb. 25, 1985),2475-2482.

Hoan, Nguyen , et al., "Synthesis from o-halogenated anisoles and phenetoles", *Chemical Abstracts*, 41(20), American Chemical Society, Abstract No. 6571bg,(1947),2 Pages.

Hsiang, Yaw-Huei , et al., "Identification of Mammalian DNA Topoisomerase I as an Intracellular Target of the Anticancer Drug Camptothecin", *Cancer Research*, 48(7), (Apr. 1, 1988), 1722-1726.

Iwao, Masatomo , et al., "A Regiospecific Synthesis of Carbazones via Consecutive Palladium-Catalyzed Cross-coupling and Aryne-Mediated Cyclization", *Heterocycles*, 36, (1993), 1483-1488.

Izmail'Skii, V. A., et al., "Absorption Spectra of Molecular Complexes of Derivatives of Benzacridine and Dibenzacridine", *Chemical Abstracts*, 54(8), Abstract, Column 7335b,(1960), 3 pages.

Jacob, Juergen , et al., "Monooxygenase Induction by Various Xenobiotics and its Influence on Rat Liver Microsomal Metabolism of Chrysene in Comparison to Benz[a] anthracene", *Chemical Abstracts*, 107, Abstract No. 34760, (1987),2 p.

Janin, Yves L., et al., "Synthesis and Evaluation of New 6-Amino-Substituted Benzo[c]phenanthridine Derivatives", *Journal of Medicinal Chemistry*, 36(23), (1993),3686-3692.

Jayaraman, M. , et al., "Synthesis of New Dihydroindeno ' 1,2-c I i soquinoline and Indenoisoquinoliniu Chloride Topoisomerase I Inhibitors Having High in Vivo Anticancer Activity in the Hollow Fiber Animal Model", *Journal of Medicinal Chemistry*, 45(1), (Jan. 3, 2002),242-249.

Kametani, Tetsuji , et al., "Studies on the synthesis of heterocyclic compounds. DCXXVII. The formation of 2,3, 9,10-tetramethoxybenz[c]acridine by treatment of 6,7-dimethoxy-1-(4,5-dimethoxy-2-nitrophen ethyl)-2methylisoquinoline with triethyl phosphite", *Chemical and Pharmaceutical Bulletin*, 23(9), (1975),2025-2028.

Kametani, T. , et al., "Synthesis of Heterocyclic Compounds. DCXXVII. Formation of 2,3,9,10-tetramethoxybenz[c]

acridine by treatment of 6,7-dimethoxy-1-(4,5-dimethoxy-2-nitrophenethyl)-2-methylisoquinoline with Triethyl Phosphite", *Chemical Abstracts*, 84, Abstract No. 43798, (1976), 1 p.

Kanmacher, I., et al., "Synthesis of Isoquino[1,2-b] quinazolines by Cycloaddition Reaction", *Chemical Abstracts*, 114, Abstract No. 207191,(1990),4 pages.

Kar, G. K., et al., "Regioselective Thermal Cyclization of 3-substituted Arylenaminoimine hydrochlorides. A convenient method for the synthesis of Functionalized Polycyclic Quinoline Derivatives", *Chemical Abstracts*, 123, Abstract No. 111828,(1995), 1 p.

Kerrigan, J.E., et al., "5H-8,9-Dimethoxy-5-(2-N,N-dimethylaminoethyl)dibenzo[c, h][1,6]naphthyridin-6-ones and Related Compounds as TOP1-Targeting Agents: Influence of Structure on the Ternary Cleavable Complex Formation", *Bioorganic and Medicinal Chemistry Letters*, 13, (2003),3395-3399.

Kessar, S V., et al., "Azasteroids. Part VII. Synthesis of 7-hydroxy-2-methoxy-7,8,9,10-tetrahydrobenzo[i] phenanthridine", *J. Chem Soc.*, (1971),259-261.

Kessar, S. V., et al., "New Routes to Condensed Polynuclear Compounds: Part X-Synthesis of Some Benzo[i] phenanthridines through Benzyne Cyclization", *Indian Journal of Chemistry*, 11, (Jul. 1973),pp. 624-627.

Kim, J. S., et al., "Influence of steric factors on topoisomerase I inhibition and cytotoxicity of bisbenzimidazoles related to Hoechst 33342", *Proceedings of the 86th Annual Meeting of the American Association for Cancer Research*, 36, Abstract No. 2689, Toronto, Ontario, Canada,(Mar. 1995), p. 451.

Kim, J. S., et al., "Influence of steric factors on topoisomerase I inhibition and cytotoxicity of bisbenzimidazoles related to Hoechst 33342", *Abstract 7— Proceedings of the 3rd Annual Scientific Retreat of the Cancer Institute of New Jersey*, Princeton Marriott Forrestal Village,(1995),p. 28.

Kim, Jung S., et al., "Quantitative structure-activity relationships on 5-substituted terbenzimidazoles as topoisomerase I poisons and antitumor agents", *Bioorganic& Medicinal Chemistry*, 6(2), (1998),4 pages.

Kim, J. S., et al., "Steric factors associated with the topoisomerase I inhibition and cytotoxicity of substituted bisbenzimidazoles", *Abstract 10- Proceedings of the American Association of Pharmaceutical Scientists Eastern Regional Meeting*, (1995),p. 27.

Kim, Jung S., et al., "Structure-activity Relationships of Benzimidazoles and Related Heterocycles as Topoisomerase I Poisons", *Bioorganic & Med. Chem.*, 4, (1996),pp. 621-630.

Kim, Jung S., et al., "Terbenzimidazoles: influence of 2"-, 4-, and 5-substituents on cytotoxicity and relative potency as topoisomerase I poisons, *Journal of Medicinal Chemistry*, 40(18), (Aug. 29, 1997),2818-2824.

Kitamura, Tsugio, et al., "Isoquinoline derivatives from the Ritter-type reaction of vinyl cations", *Chemical Abstracts*, 102(1), Abstract No. 6157c,(Jan. 7, 1985).

Klopman, Gilles, et al., "Testing by Artificial Intelligence: Computational Alternatives to the Determination of Mutagenicity", *Chemical Abstracts*, 118, Abstract No. 17489,(1993),1 p.

Knab, A. M., et al., "Mechanisms of Camptothecin Resistance in Yeast DNA Topoisomerase I Mutants", *Journal of Biological Chemistry*, 268(30), (Oct. 25, 1993), 22322-22330.

Lavoie, E. J., et al., "Structure-activity studies related to minor groove-binding ligands which inhibit mammalian DNA topoisomerase I", *Abstract 1—Proceedings of the 85th Annual Meeting of American Association for Cancer Research*, San Francisco, CA,(Apr. 1994),p. 2699.

Lee, Jeremy S., et al., "Coralyne binds tightly to both T.cntdot.A.cntdot.T- and C.cntdot.G.cntdot.C+-containing DNA triplexes", *Biochemistry*, 32(21), (Jun. 1, 1993),5591-5597.

Liu, Leroy F., et al., "Cleavage of DNA by Mammalian DNA Topoisomerase II", *Journal of Biological Chemistry*, vol. 258, No. 24, (Dec. 25, 1983), 15365-15370.

Meegalla, Sanath K., et al., "Synthesis and Pharmacological Evaluation of Isoindolo[1,2-b]quinazolinone and Isoindolo [2, 1-a]benzimidazole Derivatives Related to the Antitumor Agent Batracylin", *J. Med. Chem.*, 37, (1994),pp. 3434-3439.

Memetzidis, G., et al., "Structure-affinity relationships of berbines or 5,6,13a-tetrahydro-8H-dibenzo[a,g]quinolizines at.alpha.-adrenoceptors", *European Journal of Medicinal Chemistry*, 26, (1991),605-611.

Messmer, F. M., et al., "Fagaronine, a New Tumor Inhibitor Isolated from Fagara zanthoxyloides Lam. (Rutaceae)", *Journal of Pharmaceutical Sciences*, (Nov. 1972), 1858-1859.

Mohanty, M., et al., "New Therapeutic agents of the quinoline series. I. Fused quinolyl compounds", *Chemical Abstracts*, (Jul. 29, 1968),p. 1792.

Nelson, Janis T., et al., "Proton and carbon-13 NMR spectra of fifteen substituted isoquinolines", *Chemical Abstracts*, 115(5), Abstract No. 048721,(Aug. 5, 1991),753.

Peters, Dan, et al., "Synthesis of Various 5-Substituted Uracils", *Journal of Heterocyclic Chemistry*, 27, (Nov.-Dec. 1990),2165-2173.

Pilch, Daniel S., et al., "A terbenzimidazole that perferentially binds and conformationally alters structurally distinct DNA duplex domains: a potential mechanism for topoisomerase I poisoning", *Proc. Nat'l. Acad. Sci. USA*, 94(25), (Dec. 1997), 13565-13570.

Pilch, Daniel S., et al., "Biophysical Characterization of a Cytotoxic, Topoisomerase I Poison", *Abstract 8—Proceedings of the 3rd Annual Scientific Retreat of the Cancer Institute of New Jersey*, Princeton Marriott Forrestal Village, Princeton, NJ,(Jun. 1, 1995), p. 3..

Pilch, Daniel S., et al., "Characterizing the DNA binding modes of a topoisomerase I-poisoning terbenzimidazole: evidence for both intercalative and minor groove binding properties", *Drug Design and Discovery*, 13, (Apr. 1996), 115-133.

Piper, J. R., et al., "Synthesis and Antifolate Activity of 5-Methyl-5, 10-dideaza Analogues of Aminopterin and Folic Acid and an Alternative Synthesis of 5, 10-Dideazatetrahydrofolic Acid, a Potent Inhibitor of Glycinamide Ribonucleotide Formyltransferase", *J. Med. Chem.*, 31, (1988),pp. 2164-2169.

Porai-Koshits, B. A., et al., "Imidazole derivatives Synthesis of some polybenzimidazoles", *J. Gen. Chem. USSR*, 23, As related in Chemical Abstracts, 48 (10) (1954), Col. 12740, (1953),pp. 873-879.

Porai-Koshits, B. A., et al., "Imidazole derivatives, Synthesis of some polybenzimidazoles", *Zhur. Obshchel Khim*, 23, As related in Chemical Abstracts, 48 (1954) Col. 4523,(1953),pp. 835-841.

Quast, Ulrich, et al., "Heterocyclic.alpha.-carbinolamines with the isoquinuclidine skeleton. 3. Benzoisoquinuclidines", *Chemical Abstracts*, 97 (21), Abstract No. 182180s,(Nov. 22, 1982),806.

Ramesh, D., et al., "Studies on Polycyclic Azaarenes. 2. Sythesis of Trans-3,4-dihydroxy-3,-dihydrobenz[c]acridine and trans-8,9-dihydroxy-8,9-dihydrobenz[c]acridine", *Chemical Abstracts*, 118, Abstract No. 37626,(1988), 2 pages.

Ray, Jayanta K., et al., "A Facile and Convenient Method for the Synthesis of 8-methoxy-10,11-dihydronaphtho[1,2-b]quinolines", *Chemical Abstracts*, 92, Abstract No. 76254, (1980),30-31.

Ruchelman, A. L., et al., "11H-Isoquinol[4,3-c]cinnolin-12-ones: novel anticancer agents with potent topoisomerase I-targeting activity and cytotoxicity", *Bioorganic & Medicinal Chemistry*, 12, (2004), 795-806.

Ruchelman, Alexander L., et al., "Diaza- and Triazachrysenes: Potent Topoisomerase Tareting Agents with Exceptional Antitumor Activity against the Human Tumor Xenograft", *Bioorganic& Medicinal Chemistry Letters*, vol. 12, MDA-MB-435,(Nov. 2002),3333-3336.

Safaryan, G. P., et al., "2-Benzopyrylium salts. 25, Reaction of 2-benzopyrylium salts with some nucleophiles", *Chemical Abstracts*, 96(17), Abstract No. 142656z,(Apr. 26, 1982), 739.

Schiess, P., et al., "Thermolytic ring opening of acyloxybenzocyclobutenes: an efficient route to 3-substituted isoquinolines", *Chemical Abstracts*, 104(19), Abstract No. 168332z,(May 12, 1986),639.

Sethi, Manohar L., "Enzyme Inihibition VI: Inhibition of Reverse Transcriptase Activity by Proberberine Alkaloids and Structure-Activity Relationships", *Journal of Pharmaceutical Sciences*, 72(5), (1983),538-541.

Scherbakova, I. v., et al., "2-Benzopyrilium salts. 35. Synthesis of the natural alkaloid dehydronorcoralydine and other substituted salts of dibenzo[a,g]quinolizine", *Chemical Abstracts*, 112 (19), Abstract No. 179554,(May 7, 1990), 75-80.

Shelanski, H. A., "Acute and Chronic Toxicity Tests on Electrolytic Iron Power", *Bulletin of the National Formulary Committee, XVIII* (5-6), (1950),81-112.

Singh, Malvinder P., et al., "Synthesis and Sequence-Specific DNA Binding of a Topoisomerase Inhibitory Analog of Hoechst 33258 Designed for Altered Base and Sequence Recognition", *Chem. Res. Toxicol.*, 5, (1992),pp. 597-607.

Sotomayor, N., et al., "Oxidation reactions of 2'-functionalized 3-aryltetrahydro-and 3,4-dihydroisoquinolines", *Chemical Abstracts*, 124 (11), Abstract No. 145854,(Mar. 11, 1996),p. 1227.

Southard, G. L., et al., "Drug Delivery Devices", *USPATFULL Database, No. 91:36238, RN No. 218-38-2 (Benzo[c]phenanthradine)*, from U.S. Patent 5,013,553, (May 7, 1991),2 pages.

Studier, F. W., et al., "Use of T7 RNA polymerase to direct expression of cloned genes", *Methods in Enzymology*, 185, (1990),60-89.

Sun, Qun, et al., "Structure activity of novel topoisomerase I inhibitors related to Hoechst 33342", *Abstract 6—Proceedings of the American Association of Pharmaceutical Scientists Eastern Regional Meeting*, Hyatt Regency Hotel, New Brunswick, NJ, (Jun. 5-6, 1995),p. 25.

Sun, Qun, et al., "Structure Activity of Topoisomerase I Poisons Related to Hoechst 33342", *Bioorganic & Medicinal Chemistry Letters*, 4 (24), (1994),pp. 2871-2876.

Sun, Qun, et al., "Structure-activity studies related to minor groove-binding ligands which inhibit mammalian DNA topoisomerase I", *Cancer Institute of New Jersey's First Annual Scientific Retreat*, Abstract 2, Princeton Marriott Forrestal Village, Princeton, NJ,(Jun. 7, 1994),p. 66.

Sun, Qun, et al., "Synthesis and Evaluation of Terbenzimidazoles as Topoisomerase I Inhibitors", *Chemical Abstracts*, vol. 123, No. 15, Abstract No. 198740r,(Oct. 9, 1995), 1241.

Sun, Qun, et al., "Synthesis and Evaluation of Terbenzimidazoles as Topoisomerase I Inhibitors", *J. Med. Chem* (38), vol. 38, (1995),pp. 3638-3644.

Sun, Qun, et al., "Synthesis and Pharmacological Evaluation of a Series of Novel DNA Topoisomerase I Inhibitors as Antitumor Agents", *Scientific Proceedings of 86th Annual Meeting of the American Association for Cancer Research*, Abstract 3, vol. 36, Toronto, Canada,(Mar. 1995).

Sun, Qun, et al., "Synthesis and pharmacological evaluation of a series of novel DNA topoisomerase I inhibitors as antitumor agents", *Abstract 5—Proceedings of the 3rd Annual Scientific Retreat of the Cancer Institute of New Jersey*, Princeton Marriott Forrestal Village, Princeton, NJ,(1995),p. 27.

Sun, Qun, et al., "Synthesis of Benzimidazo[2,1-a] isoquinolines and 5,6-Dihydrobenzimidazo[2,1-a] isoquinolines", *Syn. Lett., submitted*, Paper No. 7,(1995),6 p.

Tamura, H., et al., "Molecular cloning of a cDNA of a camptothecin-resistant human DNA topoisomerase I and identification of mutation sites", *Nucleic Acids Research*, 19 (*1*), (Jan. 11, 1991),pp. 69-75.

Vinogradov, A. E., et al., "Some properties of new DNA specific bisbenzimidazole fluorochromes without a piperazine ring", *Biotechnic & Histochemistry*, 38 (5), (1993),pp. 265-269.

Walterova, D., et al., "Isolation, Chemistry and Biology of Alkaloids from plants of Papaveraceae. Part XCV. Practical application of isotachophoresis in analysis of isoquinoline alkaloids", *Chemical Abstract*, vol. 104, No. 12, (1986),254.

Wang, Li-Kai, et al., "Inhibition of Topoisomerase I Function by Coralyne and 5,6-Dihydrocoralyne", *Chem. Res. Toxicol.*, 9, (1996),pp. 75-83.

Wang, Li-Kai, et al., "Inhibition of Topoisomerase I Function by Nitidine and Fagaronine", *Chem. Res. Toxicol.*, 6, (1993),pp. 813-818.

Waters, W. A., et al., "Reactions of Free Benzyl Radicals with Benz[a]- and Benz[c]acridine", *Chemical Abstracts*, 54(4), Abstract, Column 3424b,(1960).

Wilson, W. D., et al., "Coralyne. Intercalation with DNA as a Possible Mechanism of Antileukemic Action", *Journal of Medicinal Chemistry*, 19(*10*), Communications to the Editor,(Oct. 1976),1261-1263.

Yadagiri, Bathini, et al., "Convenient Routes to Substituted Benzimidazoles and Imidazolo[4,5-b]Pyridines Using Nitrobenzene as Oxidant", *Synthetic Communications*, 20 (*7*), (1990),pp. 955-963.

Yamamoto, Yutaka, et al., "Reaction of 6H-1, 3-oxazin-6-one with benzyne giving isoquinoline derivatives", *Chemical Abstracts*, 118 (*7*), Abstract No. 059563u,(Feb. 15, 1993),831.

Zee-Cheng, K., et al., "Experimental Antileukemic Agents. Coralyne, Analogs, and Related Compounds", *Journal of Medicinal Chemistry, 17*(3), (Feb. 1974),347-351.

Zee-Cheng, K. Y., et al., "Practical Preparation of Coralyne Chloride", *Journal of Pharmaceutical Sciences, 61* (6), (Jun. 1972),969-971.

Zee-Cheng, R. K., et al., "Tetramethoxy-dibenzoquinolizinium Salts. Preparation and Antileukemic Activity of Some Positional and Structural Isomers of Coralyne", *Journal of Medicinal Chemistry, 19*(7), (Jul. 1976),882-886.

* cited by examiner

1

2

3

4a  R = NO₂
4b  R = NH₂

5a R = NO₂
5b R = NH₂

6a R = NO₂
6b R = NH₂

8a R₁=R₂=R₃=H
8b R₁ = NO₂; R₂=H; R₃=H
8c R₁ = H; R₂ = NO₂; R₃ = H
8d R₁ = H; R₂ = H; R₃ = NO₂

3, 4a, 5a, 6a 4b, 5b, 6b

NITRO AND AMINO SUBSTITUTED TOPOISOMERASE AGENTS

PRIORITY OF INVENTION

This application claims priority to U.S. Provisional Patent Application No. 60/402,138, filed Aug. 09, 2002.

GOVERNMENT FUNDING

The invention described herein was made with government support under Grant Numbers CA39662 and CA077433 from the National Cancer Institute. The United States Government has certain rights in the invention.

BACKGROUND OF THE INVENTION

DNA-topoisomerases are enzymes which are present in the nuclei of cells where they catalyze the breaking and rejoining of DNA strands, which control the topological state of DNA. Recent studies also suggest that topoisomerases are also involved in regulating template supercoiling during RNA transcription. There are two major classes of mammalian topoisomerases. DNA-topoisomerase-I catalyzes changes in the topological state of duplex DNA by performing transient single-strand breakage-union cycles. In contrast, mammalian topoisomerase II alters the topology of DNA by causing a transient enzyme bridged double-strand break, followed by strand passing and resealing. Mammalian topoisomerase II has been further classified as Type II α and Type II β. The antitumor activity associated with agents that are topoisomerase poisons is associated with their ability to stabilize the enzyme-DNA cleavable complex. This drug-induced stabilization of the enzyme-DNA cleavable complex effectively converts the enzyme into a cellular poison.

Several antitumor agents in clinical use have potent activity as mammalian topoisomerase II poisons. These include adriamycin, actinomycin D, daunomycin, VP-16, and VM-26 (teniposide or epipodophyllotoxin). In contrast to the number of clinical and experimental drugs which act as topoisomerase II poisons, there are currently only a limited number of agents which have been identified as topoisomerase I poisons. Camptothecin and its structurally-related analogs are among the most extensively studied topoisomerase I poisons. Recently, bi- and terbenzimidazoles (Chen et al., Cancer Res. 1993, 53, 1332–1335; Sun et al., J. Med. Chem. 1995, 38, 3638–3644; Kim et al., J. Med. Chem. 1996, 39, 992–998), certain benzo[c]phenanthridine and protoberberine alkaloids and their synthetic analogs (Makhey et al., Med. Chem. Res. 1995, 5, 1–12; Janin et al., J. Med. Chem. 1975, 18, 708–713; Makhey et al., Bioorg. & Med. Chem. 1996, 4, 781–791), as well as the fungal metabolites, bulgarein (Fujii et al., J. Biol. Chem. 1993, 268, 13160–13165) and saintopin (Yamashita et al., Biochemistry 1991, 30, 5838–5845) and indolocarbazoles (Yamashita et al., Biochemistry 1992, 31, 12069–12075) have been identified as topoisomerase I poisons. Other topoisomerase poisons have been identified including certain benzo[i]phenanthridine and cinnoline compounds (see LaVoie et al., U.S. Pat. No. 6,140,328 and WO 01/32631). Despite these reports there is currently a need for additional agents that are useful for treating cancer.

SUMMARY OF THE INVENTION

Applicant has discovered compounds that show inhibitory activity against topoisomerase I and/or topoisomerase II, and compounds that are effective cytotoxic agents against cancer cells, including drug-resistant cancer cells. Accordingly, the invention provides a compound of the invention which is a compound of formula I:

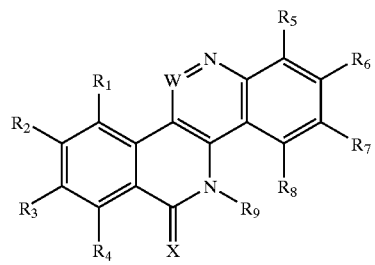

wherein:
one of $R_1$, $R_2$ and $R_3$ is nitro or $NR_aR_b$;
and the remaining $R_1$, $R_2$, and $R_3$ are each independently hydrogen, $(C_1-C_6)$alkyl, $(C_3-C_6)$cycloalkyl, $NR_aR_b$, $COOR_c$, $OR_d$; or $R_1$ and $R_2$, or $R_2$ and $R_3$ taken together are methylenedioxy, 1,2-ethylenedioxy, or 1,3-propylenedioxy;
$R_4$ is hydrogen, hydroxy, or fluoro;
each $R_5$, $R_6$, $R_7$, and $R_8$ is independently hydrogen, $(C_1-C_6)$alkyl, $(C_3-C_6)$cycloalkyl, $NR_aR_b$, $COOR_c$, $OR_d$; or $R_5$ and $R_6$, $R_6$ and $R_7$, or $R_7$ and $R_8$ taken together are methylenedioxy, 1,2-ethylenedioxy, or 1,3-propylenedioxy;
$R_9$ is $(C_1-C_6)$alkyl substituted with one or more (e.g. 1, 2, 3, or 4) solubilizing groups;
W is N or CH;
X is two hydrogens, =O, =S, or =$NR_e$;
$R_a$ and $R_b$ are each independently hydrogen or $(C_1-C_6)$ alkyl, or $R_a$ and $R_b$ together with the nitrogen to which they are attached form a pyrrolidino, piperidino or morpholino ring;
each $R_c$ is hydrogen, $(C_1-C_6)$alkyl, aryl, or aryl$(C_1-C_6)$alkyl;
each $R_d$ is hydrogen, $(C_1-C_6)$alkyl, $(C_1-C_6)$alkanoyl, aryl, or aryl$(C_1-C_6)$alkyl; and
$R_e$ is hydrogen, $(C_1-C6)$alkyl, aryl, or aryl$(C_1-C_6)$alkyl;
or a pharmaceutically acceptable salt thereof.

The invention also provides a pharmaceutical composition comprising a effective amount of a compound of the invention in combination with a pharmaceutically acceptable diluent or carrier.

The invention also provides a method of inhibiting cancer cell growth, comprising administering to a mammal afflicted with cancer, an amount of a compound of the invention, effective to inhibit the growth of said cancer cells.

The invention also provides a method comprising inhibiting cancer cell growth by contacting said cancer cell in vitro or in vivo with an amount of a compound of the invention, effective to inhibit the growth of said cancer cell.

The invention also provides a compound of the invention for use in medical therapy, preferably for use in treating cancer, for example, solid tumors, as well as the use of a compound of the invention for the manufacture of a medicament useful for the treatment of cancer, for example, solid tumors.

The invention also provides processes and novel intermediates disclosed herein which are useful for preparing compounds of the invention. Some of the compounds of formula I are useful to prepare other compounds of formula I.

DETAILED DESCRIPTION

Figure 1:
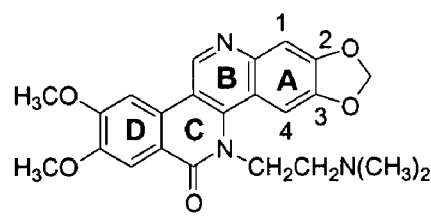
FIG. 1 shows the structure of compounds of the invention (4a, 4b, 5a, 5b, 6a, and 6b) as well as compounds 1, 2, and 3.
Figure 1:
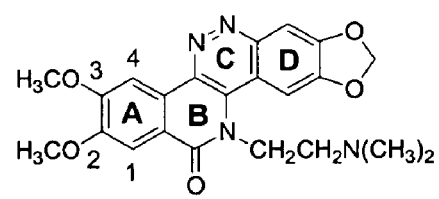
Figure 1:
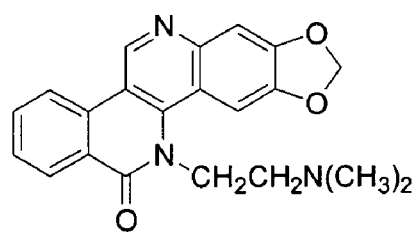
Figure 1:
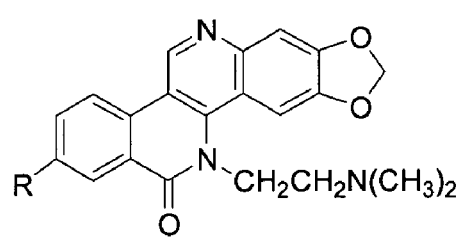
Figure 1:
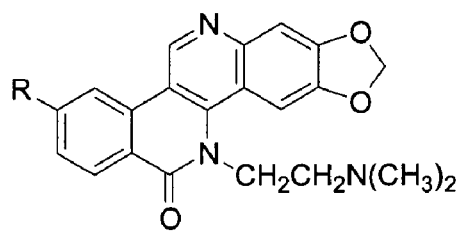
Figure 1:
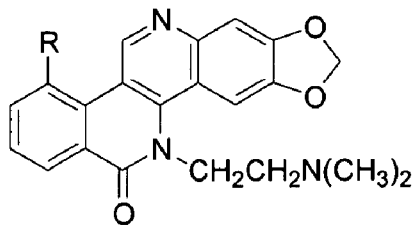

The following definitions are used, unless otherwise described.

"$(C_1-C_6)$alkyl" denotes both straight and branched carbon chains with 1, 2, 3, 4, 5, or 6, carbon atoms, but reference to an individual radical such as "propyl" embraces only the straight chain radical, a branched chain isomer such as "isopropyl" being specifically referred to.

"$(C_3-C_6)$cycloalkyl" denotes a carbocyclic ring with 3, 4, 5, or 6, carbon atoms.

"Aryl" denotes a phenyl radical or an ortho-fused bicyclic carbocyclic radical having about nine to ten ring atoms in which at least one ring is aromatic. Examples of aryl include phenyl, indenyl, and naphthyl.

"Aryl$(C_1-C_6)$alkyl" refers to a group of the formula aryl-$(C_1-C_6)$alkyl-, where aryl and $(C_1-C_6)$alkyl are as defined herein.

1. "Solubilizing group ($R_z$)" is a substituent that increases the water solubility of the compound of formula I compared to the corresponding compound lacking the $R_z$ substituent (i.e. wherein $R_z$ is hydrogen). Examples of solubilizing groups include $(C_1-C_6)$alkoxycarbonyl (e.g.—$CO_2Me$), cyano, halo, hydroxy, mercapto, oxo (=O), carboxy (COOH), nitro, pyrrolidinyl, piperidinyl, imidazolidinyl, imidazolinyl, piperazinyl, morpholinyl, thiomorpholinyl, and —$NR_fR_g$, wherein $R_f$ and $R_g$ may be the same or different and are chosen from hydrogen, $(C_1-C_6)$alkyl, and $(C_3-C_6)$cycloalkyl.

Specific and preferred values listed below for radicals, substituents, and ranges, are for illustration only; they do not exclude other defined values or other values within defined ranges for the radicals and substituents.

A specific value for W is N.
Another specific value for W is CH.
A specific value for $R_1$ is nitro.
Another specific value for $R_1$ is $NR_aR_b$.
A specific compound of formula (I) is a compound wherein $R_2$ and $R_3$ are each independently hydrogen, or $OR_d$, wherein each $R_d$ is hydrogen or $(C_1-C_6)$alkyl.
A specific compound of formula (I) is a compound wherein $R_2$ and $R_3$ are each hydrogen.
A specific value for $R_2$ is nitro or $NR_aR_b$.
Another specific value for $R_2$ is nitro.
Another specific value for $R_2$ is $NR_aR_b$.
A specific compound of formula (I) is a compound wherein $R_1$ and $R_3$ are each independently hydrogen, or $OR_d$, wherein each $R_d$ is hydrogen or $(C_1-C_6)$alkyl.

A specific compound of formula (I) is a compound wherein $R_1$ and $R_3$ are each hydrogen.
A specific value for $R_3$ is nitro or $NR_aR_b$.
Another specific value for $R_3$ is nitro.
Another specific value for $R_3$ is $NR_aR_b$.
A specific compound of formula (I) is a compound wherein $R_1$ and $R_2$ are each independently hydrogen, or $OR_d$, wherein each $R_d$ is hydrogen or $(C_1-C_6)$alkyl.
A specific compound of formula (I) is a compound wherein $R_1$ and $R_2$ are each hydrogen.
A specific value for $R_4$ is hydrogen.
Another specific value for $R_4$ is fluoro or hydroxy.
A specific compound of formula (I) is a compound wherein one of $R_2$ and $R_3$ is nitro or $NR_aR_b$.
A specific compound of formula (I) is a compound wherein each $R_5$, $R_6$, $R_7$, and $R_8$ is independently hydrogen, or $OR_d$.
A specific value for $R_5$ is hydrogen.
A specific value for $R_6$ $OR_d$.
A specific value for $R_7$ $OR_d$.
A specific value for $R_8$ is hydrogen.
A specific compound of formula (I) is a compound wherein or $R_5$ and $R_6$ taken together are methylenedioxy, 1,2-ethylenedioxy, or 1,3-propylenedioxy.
A specific compound of formula (I) is a compound wherein or $R_6$ and $R_7$ taken together are methylenedioxy, 1,2-ethylenedioxy, or 1,3-propylenedioxy.
A specific compound of formula (I) is a compound wherein $R_7$ and $R_8$ taken together are methylenedioxy, 1,2-ethylenedioxy, or 1,3-propylenedioxy.
A specific value for $R_9$ is $(C_1-C_6)$alkyl substituted with one or more hydroxy groups.
Another specific value for $R_9$ is $(C_1-C_6)$alkyl substituted with one hydroxy group.
Another specific value for $R_9$ is $(C_1-C_6)$alkyl substituted with one or more mercapto groups.
Another specific value for $R_9$ is $(C_1-C_6)$alkyl substituted with one mercapto group.
Another specific value for $R_9$ is $(C_1-C_6)$alkyl substituted with one or more carboxy groups.
Another specific value for $R_9$ is $(C_1-C_6)$alkyl substituted with one carboxy group.
Another specific value for $R_9$ is $(C_1-C_6)$alkyl substituted with one or more $NR_fR_g$ groups.
Another specific value for $R_9$ is $(C_1-C_6)$alkyl substituted with one $NR_fR_g$ group.
Another specific value for $R_9$ is $(C_1-C_6)$alkyl substituted with one or more $NH_2$ groups.
Another specific value for $R_9$ is a $(C_1-C_6)$alkyl substituted with one $NH_2$ group.
Another specific value for $R_9$ is $(C_1-C_6)$alkyl substituted with one or more $N(CH_3)_2$ groups.
Another specific value for $R_9$ is a $(C_1-C_6)$alkyl substituted with one $N(CH_3)_2$ group.
Another specific value for $R_9$ is $(C_1-C_6)$alkyl substituted with one or more $N(CH_2CH_3)_2$ groups.
Another specific value for $R_9$ is a $(C_1-C_6)$alkyl substituted with one $N(CH_2CH_3)_2$ group.
Another specific value for $R_9$ is a $(C_1-C_6)$alkyl substituted with one or more $(C_1-C_6)$alkoxycarbonyl, cyano, halo, hydroxy, mercapto, oxo, carboxy, nitro, pyrrolidinyl, piperidinyl, imidazolidinyl, imidazolinyl, piperazinyl, morpholinyl, thiomorpholinyl, or —$NR_fR_g$ groups.
Another specific value for $R_9$ is a $(C_2-C_4)$alkyl substituted with one or two groups selected from hydroxy, mercapto, carboxy, amino, methylamino, ethylamino, dimethylamino, and diethylamino.

Another specific value for $R_9$ is 2-hydroxyethyl.
Another specific value for $R_9$ is 3-hydroxypropyl.
Another specific value for $R_9$ is 2-hydroxypropyl.
Another specific value for $R_9$ is —CH$_2$CH$_2$—NR$_f$R$_g$ wherein R$_f$ and R$_g$ are each independently hydrogen or (C$_1$–C$_6$)alkyl.

Another specific value for $R_9$ is —CH$_2$CH$_2$—NR$_f$R$_g$ wherein R$_f$ and R$_g$ are each independently methyl or ethyl.

A specific compound is any one of compounds 4a, 4b, 5a, 5b, 6a, and 6b; or a pharmaceutically acceptable salt thereof.

Another specific compound is a compound of formula (I) wherein R$_1$ is hydrogen; R$_2$ is nitro; R$_3$ is hydrogen; R$_4$ is hydrogen; R$_5$ is hydrogen; R$_6$ and R$_7$ taken together are methylenedioxy; R$_8$ is hydrogen; R$_9$ is 2-(N,N-dimethylamino)ethyl or 2-(N,N-diethylamino)ethyl; W is N or CH; and X is =O; or a pharmaceutically acceptable salt thereof.

Another specific compound is a compound of formula (I) wherein R$_1$ is hydrogen; R$_2$ is hydrogen; R$_3$ is nitro; R$_4$ is hydrogen; R$_5$ is hydrogen; R$_6$ and R$_7$ taken together are methylenedioxy; R$_8$ is hydrogen; R$_9$ is 2-(N,N-dimethylamino)ethyl or 2-(N,N-diethylamino)ethyl; W is N or CH; and X is =O; or a pharmaceutically acceptable salt thereof.

Figure 2:
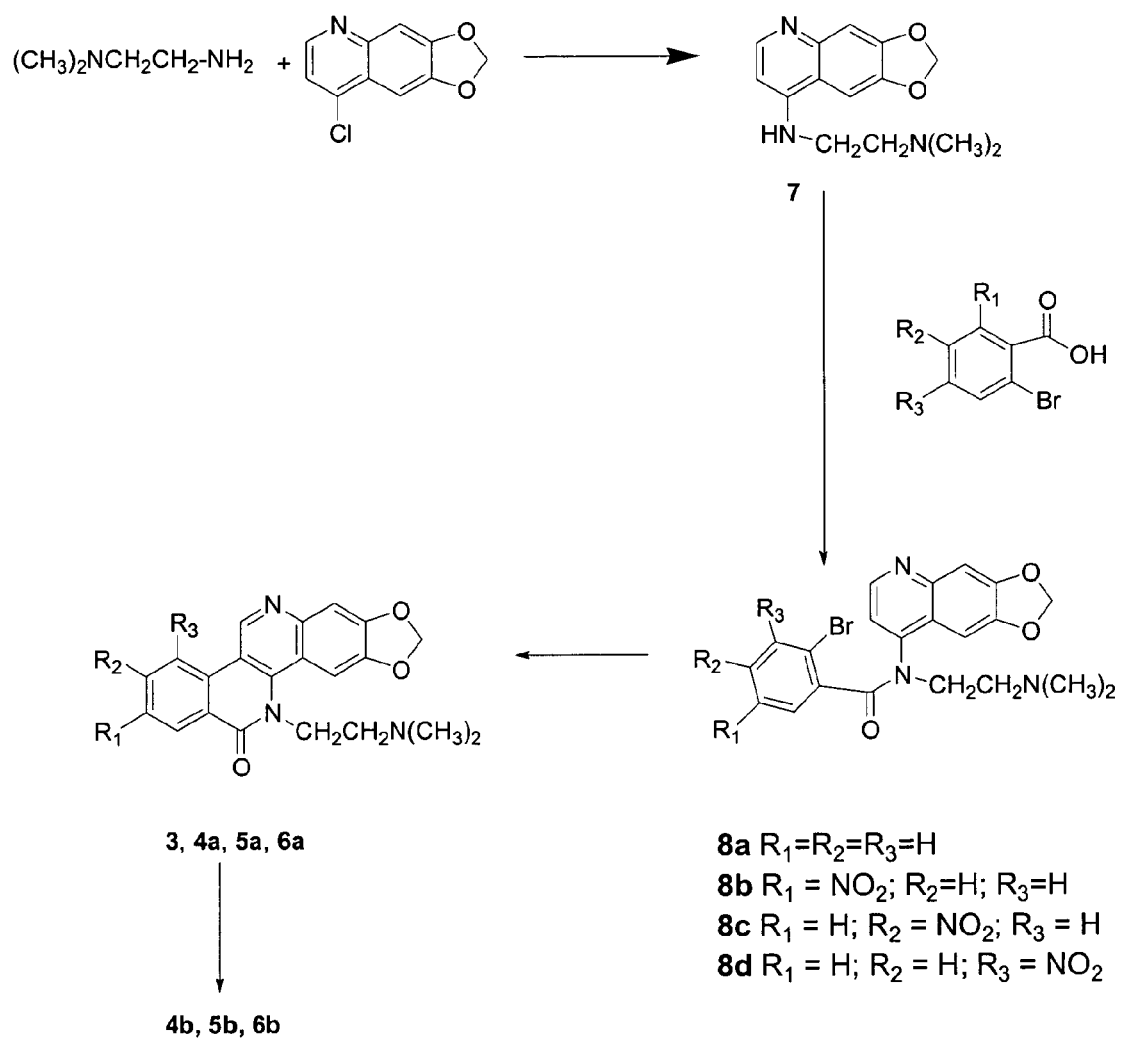
FIG. 2 illustrates the synthesis of representative compounds of formula I (4a, 4b, 5a, 5b, 6a, and 6b) and compound 3.

A compound of formula I can be prepared as described in the Examples below and as illustrated in FIG. 2. Reaction of a 4-chloroquinoline with the requisite amine provides compound 7. Amide formation provides compounds 8b–8d, which can be cyclized to provide compounds 4a–6a. Subsequent reduction of the nitro group in compounds 4a–6a provides aryl amines 4b–6b.

The starting materials employed in the synthetic methods described herein are commercially available, have been reported in the scientific literature, or can be prepared from readily available starting materials using procedures known in the field. It may be desirable to optionally use a protecting group during all or portions of the above described synthetic procedures. Such protecting groups and methods for their introduction and removal are well known in the art. See Greene, T. W.; Wutz, P. G. M. "Protecting Groups In Organic Synthesis" second edition, 1991, New York, John Wiley & Sons, Inc.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine topoisomerase inhibition activity or cytotoxic activity using the standard tests described herein, or using other similar tests which are well known in the art.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal, for example, sodium, potassium or lithium, or alkaline earth metal, for example calcium, salts of carboxylic acids can also be made.

The compounds of formula I can be formulated as pharmaceutical compositions and administered to a mammalian host, such as a human patient in a variety of forms adapted to the chosen route of administration, that is, orally or parenterally, by intravenous, intramuscular, topical or subcutaneous routes.

Thus, the present compounds may be systemically administered, for example, orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula I in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg per day, e.g., from about 1 to about 60 mg/kg of body weight per day or about 2 to 50 mg/kg per day.

The compound may conveniently be administered in unit dosage form; for example, containing 5 to 1,000 mg, conveniently 10 to 750 mg, most conveniently, 50 to 500 mg of active ingredient per unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The ability of a compound of the invention to effect topoisomerase I or II mediated DNA cleavage can be determined using pharmacological models that are well known to the art, for example, using a model like Test A described below.

Test A. Topoisomerase-Mediated DNA Cleavage Assays

Human topoisomerase I was expressed in *E. Coli* and isolated as a recombinant fusion protein using a T7 expression system as described by Gatto, B., et al., *Cancer Res.* 1996, 56, 2795–2800. Plasmid YepG was purified by the alkali lysis method followed by phenol deproteination and CsCl/ethidium isopycnic centrifugation method as described by Maniatis, T., et al., *J. Molecular Cloning, a Laboratory Manual*; Cold Spring Harbor Laboratory: Cold Spring Harbor, N.Y. 1982; pp 149–185. The end-labeling of the plasmid was accomplished by digestion with a restriction enzyme followed by end-filling with Klenow polymerase as previously described by Tewey, K. M., et al., *Science* 1984, 226, 466–468. The cleavage assays were performed as previously reported (see Gatto, B., et al., *Cancer Res.* 1996, 56, 2795–2800; and Wang, H., et al., *Biochemistry* 2001, 40; 3316–3323). The drug and the DNA in presence of topoisomerase I was incubated for 30 minutes at 37° C. The reactions were terminated by the addition of 5 $\mu$l of 5% SDS and 1 mg/ml protein kinase K with an additional 1 hour of incubation at 37° C. Samples were then alkali denatured by the addition of NaOH, EDTA, sucrose, and bromophenol blue to final concentrations of 75 mM, 2.5%, and 0.05 mg/ml, respectively, prior to loading onto a neutral agarose gel. After development of the gels, typically 24-hour exposure was used to obtain autoradiograms outlining the extent of DNA fragmentation. Topoisomerase I-mediated DNA cleavage values are reported as REC, Relative Effective Concentration, i.e. concentrations relative to topotecan, whose value is arbitrarily assumed as 1.0, that are able to produce the same cleavage on the plasmid DNA in the presence of human topoisomerase I. Data for representative compounds of the invention is provided in Table 1 below.

The cytotoxic effects of a compound of the invention can be determined using pharmacological models that are well known to the art, for example, using a model like Test B described below.

Test B. Inhibition of Cell Growth: MTT-Microtiter Plate Tetrazolinium Cytotoxicity Assay (RPMI 8402, CPT-K5 Cells)

The cytotoxicity was determined using the MTT-microtiter plate tetrazolinium cytotoxicity assay (MTA—See Mosmann, T., *J. Immunol. Methods* 1983, 65, 55–63; Carmichael, J., et al., *Cancer Res.* 1987, 47, 936–942; and Denizot, F., et al., *J. Immunol. Methods* 1986, 89, 271–277). The human lymphoblast RPMI8402 and its camptothecin-resistant variant cell line, CPT-K5 were provided by Dr. Toshiwo Andoh (Aichi Cancer Center Research Institute, Nagoya, Japan—See Andoh, T., et al., *Adv. in Pharmacology* 1994, 29B, 93–103). The cytotoxicity assay was performed using 96-well microtiter plates. Cells were grown in suspension at 37° C. in 5% $CO_2$ and maintained by regular passage in RPMI medium supplemented with 10% heat-inactivated fetal bovine serum, L-glutamine (2 mM), penicillin (100 U/mL), and streptomycin (0.1 mg/mL). Each well was plated with either 2,000 RPMI8402 cells or 4,000 CPT-K5 cells. For determination of $IC_{50}$, cells were exposed continuously for 4 days to varying concentrations of drug, and MTT assays were performed at the end of the fourth day. Each assay was performed with a control that did not contain any drug. All assays were performed at least twice in 6 replicate wells. Data for representative compounds is provided in Table 1 below.

TABLE 1

TOP1-targeting Activity and Cytotoxicity

| Compound | TOP1-mediated DNA Cleavage (REC)[a] | Cytotoxicity ($IC_{50}$; $\mu M$)[b] RPMI8402 | CPT-K5 |
|---|---|---|---|
| 1 | 0.5 | 0.002 | 0.9 |
| 2 | 0.3 | 0.001 | 0.6 |
| 3 | 6 | 0.06 | 0.95 |
| 4a | 0.2 | 0.003 | 0.33 |
| 4b | 8.0 | 0.08 | 0.38 |
| 5a | 0.1 | 0.002 | 2.8 |
| 5b | 0.5 | 0.025 | 1.0 |
| 6a | 1000 | 4.8 | >10 |
| 6b | 15 | 0.34 | 3.2 |
| Camptothecin | 0.5 | 0.005 | 61 |
| CPT-11 | 25 | 0.57 | >100 |
| Topotecan | 1 | 0.012 | >50 |
| VM-26 | >1000 | 0.22 | 0.28 |

[a]TOP1 cleavage values are reported as REC, relative effective concentration, i.e., concentrations relative to topotecan, whose value is arbitrarily assumed as 1, that produce the same degree of cleavage of the plasmid DNA in the presence of human TOP1.
[b]$IC_{50}$ was calculated after 4 days of continuous drug exposure and are the average of two or more replicate assays.

The compounds of the invention can function as cytotoxic agents against tumor cell lines, including multi-drug resistant tumor cell lines. Thus, the compounds are useful to treat cancer and can be used to treat tumors that are resistant to other specific chemotherapeutic agents.

Topoisomerase inhibitors are also known to possess antibacterial, antifungal, antiprotozoal, antihelmetic, antipsoriatic, and antiviral activity. Accordingly, the topoisomerase inhibitors of the invention may also be useful as antibacterial, antifungal, antiprotozoal, antihelmetic, antipsoritic, or antiviral agents. In particular, compounds of the invention that demonstrate little or no activity as mammalian topoisomerase I poisons, because of the possibility of similar molecular mechanism of action, could be highly active and selective antibacterial, antifungal, antiprotozoal, antihelmetic, antipsoriatic, or antiviral agents. Thus, certain compounds of the invention may be particularly useful as systemic antibacterial, antifungal, antiprotozoal, antihelmetic, antipsoriatic, or antiviral agents in mammals. The invention also provides the use of a compound of the invention for the manufacture of a medicament useful for producing an antibacterial, antifungal, antiprotozoal, antihelmetic, antipsoriatic, or antiviral effect in a mammal.

As used herein, the term "solid mammalian tumors" include cancers of the head and neck, lung, mesothelioma, mediastinum, esophagus, stomach, pancreas, hepatobiliary system, small intestine, colon, rectum, anus, kidney, ureter, bladder, prostate, urethra, penis, testis, gynecological organs, ovarian, breast, endocrine system, skin central nervous system; sarcomas of the soft tissue and bone; and melanoma of cutaneous and intraocular origin. The term "hematological malignancies" includes childhood leukemia and lymphomas, Hodgkin's disease, lymphomas of lymphocytic and cutaneous origin, acute and chronic leukemia, plasma cell neoplasm and cancers associated with AIDS. The preferred mammalian species for treatment are humans and domesticated animals.

The invention will now be illustrated by the following non-limiting Examples.

EXAMPLES

General Experimental

Melting points were determined with a Thomas-Hoover Unimelt capillary melting point apparatus. Column chromatography refers to flash chromatography conducted on Sil-iTech 32–63 $\mu m$, (ICN Biomedicals, Eschwegge, Ger.) using the solvent systems indicated. Infrared spectral data (IR) were obtained on a Perkin-Elmer 1600 Fourier transform spectrophotometer and are reported in $cm^{-1}$. Proton ($^1H$ NMR) and carbon ($^{13}C$ NMR) nuclear magnetic resonance were recorded on a Varian Gemini-200 Fourier Transform spectrometer. NMR spectra (200 MHz $^1H$ and 50 MHz $^{13}C$) were recorded in the deuterated solvent indicated with chemical shifts reported in $\delta$ units downfield from tetramethylsilane (TMS). Coupling constants are reported in hertz (Hz). Mass spectra were obtained from Washington University Resource for Biomedical and Bio-organic Mass Spectrometry within the Department of Chemistry at Washington University, St. Louis, Mo.

Example 1

8-Nitro-2,3-methylenedioxy-5-[2-(N,N-dimethylamino)ethyl]-5H-dibenzo[c,h][1,6]naphthyridin-6-one (4a).

A mixture of compound 8b (125 mg, 0.25 mmol), $Pd(OAc)_2$ (11.25 mg, 0.05 mmol), $Ag_2CO_3$ (137.5 mg, 0.5 mmol), $P(o-tolyl)_3$ (30.5 mg, 0.1 mmol) and anhyd. DMF (10 mL) was heated at 150° C. for 30 min. The reaction mixture was cooled to room temperature, filtered through Celite and washed with $CHCl_3$ (20 mL) and $CH_3OH$ (10 mL). The solvent was removed in vacuo to provide a dark solid, which was purified by flash chromatography by eluting with $CHCl_3$ and 2% methanol to give 15 mg of a yellow solid (14.4% yield); mp 219–20° C.; $^1H$ NMR ($CDCl_3$) $\delta$ 2.29 (s, 6H), 2.97 (t, 2H, J=7), 4.71 (t, 2H, J=6.8), 6.20 (s, 2H), 7.49 (s, 1H), 7.88 (s, 1H) 8.48 (d, 1H, J=8.8), 8.61 (dd, 1H, J=2.6, 9.2), 9.35 (d, 1H, J=2.2), 9.47 (s, 1H); $^{13}C$ NMR($CDCl_3$) $\delta$ 45.6, 49.6, 57.4, 101.3, 102.5, 107.3, 110.5, 114.6, 122.7, 124.9, 125.7, 127.2, 137.7, 143.4, 143.9, 147.2, 148.2, 148.8, 151.2, 163.3; HRMS m/z calcd for $C_{21}H_{18}N_5O_5H$: 407.1356. found 407.1369.

The intermediate compound 8b was prepared as follows.

a. N'-(6,7-Methylenedioxyquinolin-4-yl)-N,N-dimethylethane-1,2-diamine (7).

The requisite chloroquiniline was stirred in refluxing phenol (5.5 mol equiv.) for 2.5 h. The temperature was lowered to 100° C. and N,N-dimethylethylenediamine (2.55 g, 29 mmol) was added with stirring. The reaction was allowed to stir at 100° C. for 24 hours and the phenol was removed by Kugelrohr distillation under reduced pressure. The residue was partitioned between $CHCl_3$ and 10% NaOH. The aqueous layer was repeatedly extracted with $CHCl_3$. All of the $CHCl_3$ solutions (initial partition and extracts) were combined and dried ($MgSO_4$) to provide compound 7 in 54% yield; mp 193–194° C.; $^1$H NMR ($CDCl_3$) δ 2.32 (s, 6H), 2.70 (t, 2H, J=6.6), 3.29 (m, 2H), 5.62 (br, 1H), 6.10 (s, 2H), 6.36 (d, 1H, J=5.3), 7.10 (s, 1H), 7.34 (s, 1H), 8.40 (d, 1H, J=5.3); $^{13}$C NMR ($CDCl_3$) δ 40.1, 45.2, 57.2, 96.3, 98.9, 101.6, 106.5, 114.4, 145.2, 146.8, 148.9, 149.7,150.1; HRMS calcd for $C_{14}H_{17}N_3O_2$: 260.1399. found 260.1377.

b. N-(6,7-Methylenedioxyquinolin-4-yl)-N-(N,N-dimethylaminoethyl)-2-bromo-5-nitrobenzamide (8b).

To a solution of compound 7 (259 mg, 1.0 mmol) and triethylamine (0.5 mL) in dry $CH_2Cl_2$ (20 mL) was added a solution of 2-bromo-5-nitrobenzoic acid chloride in 20 mL of $CH_2Cl_2$ (which was prepared by refluxing of 295 mg, 1.2 mmol of 2-bromo-5-nitrobenzoic acid in 10 mL of thionyl chloride for 3 h.) and reaction mixture was heated to reflux for 4 h. The reaction mixture was washed with saturated $NaHCO_3$ solution, water and brine and dried over $Na_2SO_4$. The solvent was removed in vacuo to give a yellow solid; yield 350 mg (71.8%); mp 204–5° C.; $^1$H NMR ($CDCl_3$) δ (2.3, s, 6H), 2.53–2.64 (m, 2H), 3.67–3.81 (m, 1H), 4.42–4.55 (m, 1H), 6.19 (s, 2H), 7.31 (s, 1H), 7.34 (d, 1H, J=4.8), 7.43 (s, 1H), 7.52 (d, 1H, J=8.8), 7.76 (dd, 1H, J=2.6, 8.4), 7.87 (d, 1H, J=2.6), 8.53 (d, 1H, J=4.8); $^{13}$C NMR ($CDCl_3$) δ 45.4, 46.6, 56.4, 97.9, 102.4, 106.6, 119.4, 122.3, 122.8, 124.6, 127.2, 134.0, 139.0, 144.5, 145.9, 148.1, 148.5, 149.6, 151.5, 166.5.

Example 2

8-Amino-2,3-methylenedioxy-5-[2-(N,N-dimethylamino)ethyl]-5H-dibenzo[c,h][1,6]naphthyridin-6-one (4b)

To a solution of compound 4a (40 mg, 0.1 mmol) in ethanol (10 mL), Ra—Ni (~50 mg) then hydrazine hydrate (0.2 mL) were added and the reaction stirred at room temperature for 3 h. The catalyst was filtered through the Celite and filtrate was concentrated in vacuo to provide 26 mg of a solid (69.1% yield); mp 245–246° C.; $^1$H NMR ($CDCl_3$) δ 2.36 (s, 6H), 3.01 (t, 2H, J=7.4), 4.11(s, 2H), 4.68 (t, 2H, J=7.4), 6.17(s, 2H,), 7.18 (dd, 1H, J=2.8, 11.4), 7.46 (s, 1H) 7.71 (d, 1H, J=3), 7.80 (s, 1H) 8.20 (d, 1H, J=8.8), 9.40 (s, 1H); HRMS m/z calcd for $C_{21}H_{20}N_4O_3H$: 377.1614. found 377.1604.

Example 3

9-Nitro-2,3-methylenedioxy-5-[2-(N,N-Dimethylamino)Ethyl]-5H-dibenzo[c,h][1,6]naphthyridin-6-one (5a).

A mixture of compound 8c (125 mg, 0.25 mmol), Pd(OAc)$_2$ (11.25 mg, 0.05 mmol), $Ag_2CO_3$ (137.5 mg, 0.5 mmol), P(o-tolyl)$_3$ (30.5 mg, 0.1 mmol) and anhyd. DMF (10 mL) was heated at 150° C. for 2 h. The reaction mixture was cooled to room temperature, filtered through Celite, and washed with $CHCl_3$ (20 mL) and $CH_3OH$ (10 mL). The solvent was removed in vacuo to provide a dark solid, which was purified by flash chromatography by eluting with $CHCl_3$ and 1% methanol to provide 40 mg of a yellow solid in 38.4% yield; mp 258–259° C.; $^1$H NMR ($CDCl_3$) δ 2.28 (s, 6H), 2.96 (t, 2H, J=6.4), 4.71 (t, 2H, J=6.6), 6.22 (s, 2H) 7.52 (s, 1H), 7.88 (s, 1H), 8.37 (dd, 1H, J=1.8, 8.6), 8.66 (d, 1H, J=8.8), 9.22 (d, 1H, J=1.8), 9.51 (s, 1H); $^{13}$C NMR ($CDCl_3$) δ 45.6, 49.6, 57.2, 101.1, 102.5, 107.3, 110.8, 114.6, 117.0, 121.9, 128.8, 130.9, 133.9, 142.6, 143.4, 148.2, 148.6, 150.9, 151.0, 163.3; HRMS m/z calcd for $C_{21}H_{18}N_4O_5H$: 407.1356. found 407.1339.

The intermediate compound 8c was prepared as follows.

a. N-(6,7-Methylenedioxyquinolin-4-yl)-N-(N,N-dimethylaminoethyl)-2-bromo-4-nitrobenzamide (8c).

To a solution of compound 7 (259 mg, 1.0 mmol) and triethylamine (0.5 mL) in dry $CH_2Cl_2$ (20 mL) was added a solution of 2-bromo-4-nitrobenzoic acid chloride in 20 mL of $CH_2Cl_2$ (which was prepared by refluxing of 295 mg, 1.2 mmol of 2-bromo-4-nitrobenzoic acid in 10 mL of thionyl chloride for 4 h). The reaction mixture was heated to reflux for 6 h. The reaction mixture was allowed to cool and was then washed with saturated $NaHCO_3$ solution, water and brine and dried over anhydrous $Na_2SO_4$. The solvent was then removed in vacuo to give a yellow solid; yield 345 mg (70.8%); mp 111–112° C.; $^1$H NMR ($CDCl_3$) δ (2.29, S, 6H), 2.60 (t, 2H, J=6.2), 3.62–3.72 (m, 1H), 4.49–4.62 (m, 1H), 6.19 (d, 2H, J=5.6), 7.12 (d, 1H, J=8.2), 7.37 (s, 3H), 7.75 (d, 1H, J=8) 8.26 (s, 1H), 8.5 (d, 1H, J=4.6); $^{13}$C NMR ($CDCl_3$) δ 45.4, 46.6, 56.4, 97.8, 102.4, 106.7, 119.5, 120.6, 121.7, 122.7, 127.6, 128.1, 143.6, 144.4, 147.9, 148.2, 148.5, 149.5, 151.4, 166.8.

Example 4

9-Amino-2,3-methylenedioxy-5-[2-(N,N-dimethylamino)ethyl]-5H-dibenzo[c,h][1,6]naphthyridin-6-one (5b).

To a solution of compound 5a (40 mg, 0.1 mmol) in ethanol (10 mL), Ra—Ni (~50 mg) and then hydrazine hydrate (0.2 mL) were added and the reaction stirred at room temperature for 3 h. The catalyst was filtered through Celite and filtrate was concentrated in vacuo to provide 23 mg of a solid (61.1% yield); mp 300–301° C.; $^1$H NMR ($CDCl_3$) δ 2.36 (s, 6H), 3.01 (t, 2H, J=6.6), 4.33 (s, 2H), 4.63 (t, 2H, J=7), 6.18 (s, 2H), 6.91(dd, 1H, J=2.2, 8.8), 7.46 (s, 1H), 7.45 (d, 1H, J=2.2), 7.83 (s, 1H), 8.30 (d, 1H, J=8.8), 9.35 (s, 1H); HRMS m/z calcd for $C_{21}H_{20}N_4O_3H$: 377.1614. found 377.1606.

Example 5

10-Nitro-2,3-methylenedioxy-5-[2-(N,N-dimethylamino)Ethyl]-5H-dibenzo[c,h][1,6]naphthyridin-6-one (6a).

A mixture of compound 8d (125 mg, 0.25 mmol), Pd(OAc)$_2$ (11.25 mg, 0.05 mmol), $Ag_2CO_3$ (137.5 mg, 0.5 mmol), P(o-tolyl)$_3$ (30.5 mg, 0.1 mmol) and anhyd. DMF (10 mL) was heated at 150° C. for 2 h. The reaction mixture was cooled to room temperature, filtered through Celite and washed with $CHCl_3$ (20 mL) and $CH_3OH$ (10 mL). The solvent was removed in vacuo to yield a dark solid, which was purified by flash chromatography by eluting with $CHCl_3$ and 1% methanol to provide 35 mg of a yellow solid in 33.6% yield; mp 189–90° C.; $^1H$ NMR ($CDCl_3$) δ (2.28, s, 6H), 2.90 (t, 2H, J=7), 4.69 (t, 2H, J=7), 6.20 (s, 2H), 7.44 (s, 1H), 7.67 (t, 1H, J= 8.8) 7.79 (s, 1H), 8.03 (dd, 1H, J=1.4, 8) 8.71 (dd, 1H, J=1.4, 7.6), 8.85 (s, 1H); HRMS m/z calcd for $C_{21}H_{18}N4O_5H$: 407.1356. found 407.1351.

The intermediate compound 8d was prepared as follows.

a. N-(6,7-Methylenedioxyquinolin-4-yl)-N-(N,N-dimethylaminoethyl)-2-bromo-3-nitrobenzamide (8d).

To a solution of compound 7 (259 mg, 1.0 mmol) and triethylamine (0.5 mL) in dry $CH_2Cl_2$ (20 mL) was added a solution of 2-bromo-3-nitrobenzoic acid chloride in 20 mL of $CH_2Cl_2$ (which was prepared by refluxing of 295 mg, 1.2 mmol of 2-bromo-3-nitrobenzoic acid in 10 mL of thionyl chloride for 4 h). The reaction mixture was heated to reflux for 6 h. The reaction mixture was allowed to cool and then washed with saturated $NaHCO_3$ solution, water and brine and dried over $Na_2SO_4$. Solvent was removed in vacuo to give 360 mg of a yellow solid (73.9%); mp 96–97° C.; $^1H$ NMR ($CDCl_3$) δ 2.30 (s, 6H), 2.62 (t, 2H, J=6.6), 3.59–3.69 (m, 1H), 4.53–4.67 (m, 1H), 6.18 (d, 2H, J=5.2), 7.05 (d, 1H, J=7.8), 7.14 (d, 1H, J=7.4) 7.28–7.36 (m, 3H) 7.50 (dd, 1H, J=1.2, 7.8), 8.55 (d, 1H, J=3.8); $^{13}C$ NMR ($CDCl_3$) δ 45.4, 46.5, 56.4, 97.8, 102.3, 106.7, 112.2, 119.5, 122.6, 125.2, 127.7, 129.7, 140.8, 144.6, 148.3, 148.5, 149.5, 151.4, 166.9

Example 6

10-Amino-2,3-methylenedioxy-5-[2-(N,N-dimethylamino)ethyl]-5H-dibenzo[c,h][1,6]naphthyridin-6-one (6b).

To a solution of compound 6a (40 mg, 0.1 mmol) in ethanol (10 mL), Ra—Ni (~50 mg) and then hydrazine hydrate (0.2 mL) were added and reaction was stirred at room temperature for 3 h. The catalyst was filtered through the Celite and filtrate was concentrated in vacuo to provide 28 mg of a solid (74.4% yield); mp 223–224° C.; $^1H$ NMR ($CDCl_3$) δ 2.31 (s, 6H), 2.90 (t, 2H, J=7), 4.34 (s, 2H), 4.65 (t, 2H, J=7.4), 6.18 (s, 2H,), 7.16 (d, 1H, J=8), 7.4 (dd, 2H, J=7.6, 9.8) 7.74 (s, 1H), 8.02 (d, 1H, J=7.8), 10.03 (s, 1H); HRMS m/z calcd for $C_{21}H_{20}N_4O_3H$: 377.1614. found 377.1631.

Example 7

The following illustrate representative pharmaceutical dosage forms, containing a compound of formula I ('Compound X'), for therapeutic or prophylactic use in humans.

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
|  | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
|  | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
|  | 600.0 |

| (iv) Injection 1 (1 mg/ml) | mg/ml |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0 N Sodium hydroxide solution (pH adjustment to 7.0–7.5) | q.s. |
| Water for injection | q.s. ad 1 mL |

| (v) Injection 2 (10 mg/ml) | mg/ml |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 01 N Sodium hydroxide solution (pH adjustment to 7.0–7.5) | q.s. |
| Water for injection | q.s. ad 1 mL |

| (vi) Aerosol | mg/can |
|---|---|
| 'Compound X' | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

Comparative Example 1

2,3-Methylenedioxy-5-[2-(N,N-dimethylamino) ethyl]-5H-dibenzo[c,h]1,6-naphthyridin-6-one (3).

A mixture of 8a (343 mg, 0.7 mmol), Pd(OAc)$_2$ (31.5 mg, 0.14 mmol), P(o-tolyl)$_3$ (85.4 mg, 0.28 mmol), and silver carbonate (385 mg, 1.4 mmol) were heated to reflux in DMF (21 mL) and stirred under nitrogen for 15 minutes, then the mixture was cooled and diluted with chloroform, filtered through Celite, and evaporated, and the crude product was chromatographed in 197:3 chloroform-methanol, to provide 95 mg, in 38% yield; mp 200.5–202° C.; IR (CHCl$_3$) 1656; $^1H$ NMR (DMSO-d$_6$) δ 2.34 (s, 6H), 3.06 (t, 2H, J=6.5), 4.67 (t, 2H, J=6.5), 6.28 (s, 2H), 7.44 (m, 1H), 7.68 (t, 1H, J=7.6), 7.79 (s, 1H), 7.92 (td, 1H, J=7.6, J=1.4), 8.34 (dd, 1H, J=8.1, J=1.4), 8.68 (d, 1H, J=8.1), 9.63 (s, 1H); $^{13}C$ NMR (DMSO-d$_6$) δ 45.1, 47.8, 56.9, 101.6, 103.3, 107.0, 112.3, 114.7, 122.8, 125.3, 128.7, 129.3, 133.1, 134.4, 141.4, 144.7, 148.0, 148.1, 150.8, 164.4.

The intermediate compound 8a was prepared as follows.

a. N-(6,7-Methylenedioxyquinolin-4-yl)-N-(N,N-dimethylaminoethyl)-2-iodobenzamide (8a).

Oxalyl chloride (1.05 g, 8.1 mmol) was added to a solution of o-iodobenzoic acid (0.57 g, 2.3 mmol) in methylene chloride (20 mL) under nitrogen, and the stirred mixture refluxed for 4 h. The mixture was then concentrated to dryness under vacuum. The acid chloride was redissolved in methylene chloride (20 mL) and added to a solution of compound 7 and triethylamine (2.0 g, 20.0 mmol) in methylene chloride (20 mL). The reaction was stirred at reflux under nitrogen for 2 h. The mixture was then cooled and washed with a saturated solution of sodium bicarbonate (3×75 mL), and extracted into dilute HCl (3×75 mL), and the combined aqueous extracts were washed with chloroform (75 mL), made basic using 30% NaOH, then extracted with chloroform (3×75 mL). The combined organic extracts were washed with brine (100 mL), dried (anhydrous $MgSO_4$), and concentrated in vacuo, to give 795 mg, in 84% yield; IR ($CHCl_3$) 1653; $^1$H NMR ($CDCl_3$) δ 2.23 (s, 6H), 2.60 (m, 2H), 3.52 (m, 1H), 4.57 (m, 1H), 6.13 (d, 1H, J=0.7), 6.16 (d, 1H, J=0.7), 6.78 (m, 3H), 7.32 (m, 2H), 7.36 (s, 1H), 7.64 (d, 1H, J=7.6), 8.48 (d, 1H, J=4.8); $^{13}$C NMR ($CDCl_3$) δ 45.6, 46.8, 56.5, 93.9, 98.4, 102.3, 106.5, 120.2, 122.8, 126.5, 127.2, 128.3, 130.2, 139.5, 141.5, 145.6, 148.2, 149.2, 151.2, 170.0.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula I:

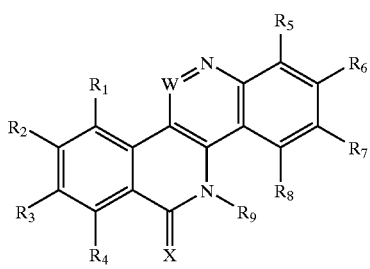

I wherein:
one of $R_1$, $R_2$ and $R_3$ is nitro or $NR_aR_b$;
and the remaining $R_1$, $R_2$, and $R_3$ are each independently hydrogen, ($C_1$–$C_6$)alkyl, ($C_3$–$C_6$)cycloalkyl, $NR_aR_b$, $COOR_c$, $OR_d$; or $R_1$ and $R_2$, or $R_2$ and $R_3$ taken together are methylenedioxy, 1,2-ethylenedioxy, or 1,3-propylenedioxy;
$R_4$ is hydrogen, hydroxy, or fluoro;
each $R_5$, $R_6$, $R_7$, and $R_8$ is independently hydrogen, ($C_1$–$C_6$)alkyl, ($C_3$–$C_6$)cycloalkyl, $NR_aR_b$, $COOR_c$, $OR_d$; or $R_5$ and $R_6$, $R_6$ and $R_7$, or $R_7$ and $R_8$ taken together are methylenedioxy, 1,2-ethylenedioxy, or 1,3-propylenedioxy;
$R_9$ is ($C_1$–$C_6$)alkyl substituted with one or more ($C_1$–$C_6$) alkoxycarbonyl, cyano, halo, hydroxy, mercapto, oxo, carboxy, nitro, pyrrolidinyl, piperidinyl, imidazolidinyl, imidazolinyl, piperazinyl, morpholinyl, thiomorpholinyl, or —$NR_fR_g$ groups, wherein $R_f$ and $R_g$ may be the same or different and are chosen from hydrogen, ($C_1$–$C_6$)alkyl, and ($C_3$–$C_6$)cycloalkyl;
W is N or CH;
X is two hydrogens, =O, =S, or =$NR_e$;

$R_a$ and $R_b$ are each independently hydrogen or ($C_1$–$C_6$) alkyl, or $R_a$ and $R_b$ together with the nitrogen to which they are attached form a pyrrolidino, piperidino or morpholino ring;
each $R_c$ is hydrogen, ($C_1$–$C_6$)alkyl, aryl, or aryl($C_1$–$C_6$) alkyl;
each $R_d$ is hydrogen, ($C_1$–$C_6$)alkyl, ($C_1$–$C_6$)alkanoyl, aryl, or aryl($C_1$–$C_6$)alkyl; and
$R_e$ is hydrogen, ($C_1$–$C_6$)alkyl, aryl, or aryl($C_1$–$C_6$)alkyl; or a pharmaceutically acceptable salt thereof.

2. The compound of claim 1 wherein W is N.
3. The compound of claim 1 wherein W is CH.
4. The compound of claim 1 wherein $R_1$ is nitro.
5. The compound of claim 1 wherein $R_1$ is $NR_aR_b$.
6. The compound of claim 1 wherein $R_2$ and $R_3$ are each independently hydrogen, or $OR_d$, wherein each $R_d$ is hydrogen or ($C_1$–$C_6$)alkyl.
7. The compound of claim 1 wherein $R_2$ and $R_3$ are each hydrogen.
8. The compound of claim 1 wherein $R_2$ is nitro or $NR_aR_b$.
9. The compound of claim 1 wherein $R_2$ is nitro.
10. The compound of claim 1 wherein $R_2$ is $NR_aR_b$.
11. The compound of claim 1 wherein $R_1$ and $R_3$ are each independently hydrogen, or $OR_d$, wherein each $R_d$ is hydrogen or ($C_1$–$C_6$)alkyl.
12. The compound of claim 1 wherein $R_1$ and $R_3$ are each hydrogen.
13. The compound of claim 1 wherein $R_3$ is nitro or $NR_aR_b$.
14. The compound of claim 1 wherein $R_3$ is nitro.
15. The compound of claim 1 wherein $R_3$ is $NR_aR_b$.
16. The compound of claim 1 wherein $R_1$ and $R_2$ are each independently hydrogen, or $OR_d$, wherein each $R_d$ is hydrogen or ($C_1$–$C_6$)alkyl.
17. The compound of claim 1 wherein $R_1$ and $R_2$ are each hydrogen.
18. The compound of claim 1 wherein $R_4$ is hydrogen.
19. The compound of claim 1 wherein $R_4$ is fluoro or hydroxy.
20. The compound of claim 1 wherein one of $R_2$ and $R_3$ is nitro or $NR_aR_b$.
21. The compound of claim 1 wherein each $R_5$, $R_6$, $R_7$, and $R_8$ is independently hydrogen, or $OR_d$.
22. The compound of claim 1 wherein $R_5$ is hydrogen.
23. The compound of claim 1 wherein each $R_6$ is $OR_d$.
24. The compound of claim 1 wherein each $R_7$ is $OR_d$.
25. The compound of claim 1 wherein each $R_8$ is hydrogen.
26. The compound of claim 1 wherein $R_5$ and $R_6$ taken together are methylenedioxy, 1,2-ethylenedioxy, or 1,3-propylenedioxy.
27. The compound of claim 1 wherein $R_6$ and $R_7$ taken together are methylenedioxy, 1,2-ethylenedioxy, or 1,3-propylenedioxy.
28. The compound of claim 1 wherein $R_7$ and $R_8$ taken together are methylenedioxy, 1,2-ethylenedioxy, or 1,3-propylenedioxy.
29. The compound of claim 1 wherein $R_9$ is ($C_1$–$C_6$)alkyl substituted with one or more hydroxy groups.
30. The compound of claim 1 wherein $R_9$ is ($C_1$–$C_6$)alkyl substituted with one hydroxy group.

31. The compound of claim 1 wherein $R_9$ is $(C_1-C_6)$alkyl substituted with one or more mercapto groups.

32. The compound of claim 1 wherein $R_9$ is $(C_1-C_6)$alkyl substituted with one mercapto group.

33. The compound of claim 1 wherein $R_9$ is $(C_1-C_6)$alkyl substituted with one or more carboxy groups.

34. The compound of claim 1 wherein $R_9$ is $(C_1-C_6)$alkyl substituted with one carboxy group.

35. The compound of claim 1 wherein $R_9$ is $(C_1-C_6)$alkyl substituted with one or more $NR_fR_g$ groups, wherein $R_f$ and $R_g$ are each independently hydrogen, $(C_1-C_6)$alkyl, or $(C_3-C_6)$cycloalkyl.

36. The compound of claim 1 wherein $R_9$ is $(C_1-C_6)$alkyl substituted with one $NR_fR_g$ group, wherein $R_f$ and $R_g$ are each independently hydrogen, $(C_1-C_6)$alkyl, or $(C_3-C_6)$ cycloalkyl.

37. The compound of claim 1 wherein $R_9$ is $(C_1-C_6)$alkyl substituted with one or more $NH_2$ groups.

38. The compound of claim 1 wherein $R_9$ is a $(C_1-C_6)$ alkyl substituted with one $NH_2$ group.

39. The compound of claim 1 wherein $R_9$ is $(C_1-C_6)$alkyl substituted with one or more $N(CH_3)_2$ groups.

40. The compound of claim 1 wherein $R_9$ is a $(C_1-C_6)$ alkyl substituted with one $N(CH_3)_2$ group.

41. The compound of claim 1 wherein $R_9$ is $(C_1-C_6)$alkyl substituted with one or more $N(CH_2CH_3)_2$ groups.

42. The compound of claim 1 wherein $R_9$ is a $(C_1-C_6)$ alkyl substituted with one $N(CH_2CH_3)_2$ group.

43. The compound of claim 1 wherein $R_9$ is a $(C_2-C_4)$ alkyl substituted with one or two groups selected from hydroxy, mercapto, carboxy, amino, methylamino, ethylamino, dimethylamino, and diethylamino.

44. The compound of claim 1 wherein $R_9$ is 2-hydroxyethyl.

45. The compound of claim 1 wherein $R_9$ is 3-hydroxypropyl.

46. The compound of claim 1 wherein $R_9$ is 2-hydroxypropyl.

47. The compound of claim 1 wherein $R_9$ is —CH$_2$CH$_2$—$NR_fR_g$ wherein $R_f$ and $R_f$ are each independently hydrogen or $(C_1-C_6)$alkyl.

48. The compound of claim 1 wherein $R_9$ is —CH$_2$CH$_2$—$NR_fR_g$ wherein $R_f$ and $R_f$ are each independently methyl or ethyl.

49. The compound of claim 1 wherein $R_1$ is hydrogen; $R_2$ is nitro; $R_3$ is hydrogen; $R_4$ is hydrogen; $R_5$ is hydrogen; $R_6$ and $R_7$ taken together are methylenedioxy; $R_8$ is hydrogen; $R_9$ is 2-(N,N-dimethylamino)ethyl or 2-(N,N-diethylamino) ethyl; W is N or CH; and X is =O; or a pharmaceutically acceptable salt thereof.

50. The compound of claim 1 wherein $R_1$ is hydrogen; $R_2$ is hydrogen; $R_3$ is nitro; $R_4$ is hydrogen; $R_5$ is hydrogen; $R_6$ and $R_7$ taken together are methylenedioxy; $R_8$ is hydrogen; $R_9$ is 2-(N,N-dimethylamino)ethyl or 2-(N,N-diethylamino) ethyl; W is N or CH; and X is =O; or a pharmaceutically acceptable salt thereof.

51. A pharmaceutical composition comprising a compound as described in claim 1 in combination with a pharmaceutically acceptable diluent or carrier.

52. A method of inhibiting cancer cell growth comprising contacting said cancer cell in vitro with an amount of a compound as described in claim 1, effective to inhibit the growth of said cancer cell.

53. The compound of claim 1 that is

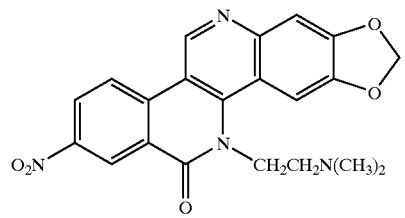

or a pharmaceutically acceptable salt thereof.

54. The compound of claim 1 that is

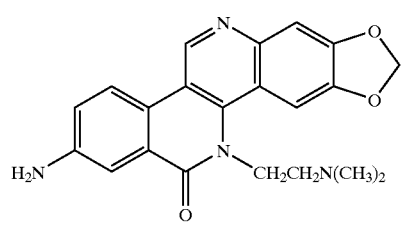

or a pharmaceutically acceptable salt thereof.

55. The compound of claim 1 that is

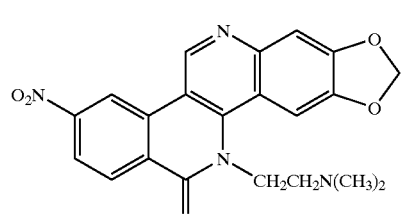

or a pharmaceutically acceptable salt thereof.

56. The compound of claim 1 that is

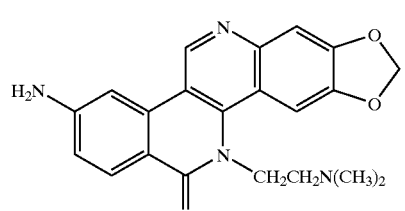

or a pharmaceutically acceptable salt thereof.

57. The compound of claim 1 that is
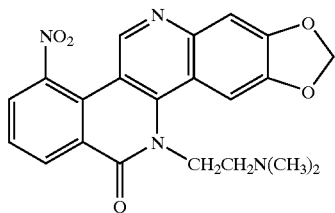
or a pharmaceutically acceptable salt thereof.
58. The compound of claim 1 that is
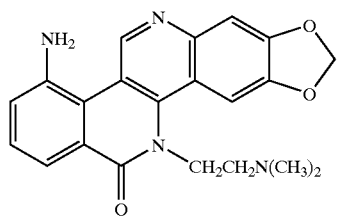
or a pharmaceutically acceptable salt thereof.
* * * * *